United States Patent
Yamasaki et al.

(10) Patent No.: US 11,688,266 B2
(45) Date of Patent: *Jun. 27, 2023

(54) HEALTH ADVISORY ALERT SYSTEMS, MOBILE COMPUTING UNITS HAVING THE SAME, AND HEALTH ADVISORY ALERT METHODS

(71) Applicant: Toyota Motor Engineering & Manufacturing North America, Inc., Plano, TX (US)

(72) Inventors: Bryan Else Yamasaki, Ypsilanti, MI (US); Timothy Wang, Ypsilanti, MI (US); Roger Akira Kyle, Frisco, TX (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/578,993

(22) Filed: Jan. 19, 2022

(65) Prior Publication Data

US 2022/0157148 A1 May 19, 2022

Related U.S. Application Data

(63) Continuation of application No. 17/097,467, filed on Nov. 13, 2020.

(51) Int. Cl.
*G08B 21/12* (2006.01)
*A61B 5/00* (2006.01)
(Continued)

(52) U.S. Cl.
CPC .............. *G08B 21/12* (2013.01); *A61B 5/742* (2013.01); *A61B 5/7405* (2013.01); *A61B 5/746* (2013.01);
(Continued)

(58) Field of Classification Search
None
See application file for complete search history.

(56) References Cited

U.S. PATENT DOCUMENTS

| | | | |
|---|---|---|---|
| 8,836,490 B2 | 9/2014 | Silzer, Sr. et al. | |
| 2019/0073618 A1* | 3/2019 | Kanukurthy | G08B 21/02 |
| 2019/0266875 A1* | 8/2019 | Herring | G08B 21/14 |

FOREIGN PATENT DOCUMENTS

| | | |
|---|---|---|
| CN | 206741671 U | 12/2017 |
| DE | 102011119544 B3 | 5/2013 |

(Continued)

*Primary Examiner* — Thomas S McCormack
(74) *Attorney, Agent, or Firm* — Dinsmore & Shohl LLP

(57) ABSTRACT

A health advisory alert system for a vehicle is presented. A controller may determine whether a vehicle occupant is preparing to exit the vehicle. Upon determination that the vehicle occupant is preparing to exit the vehicle, the controller may determine a location of the vehicle, determine a health advisory metric based on the location of the vehicle, and determine whether personal protective equipment should be worn based on the health advisory metric. Upon determination that personal protective equipment should be worn, the controller may output a notification to the vehicle occupant indicating that personal protective equipment should be worn.

19 Claims, 8 Drawing Sheets

(51) Int. Cl.
  *B60Q 9/00* (2006.01)
  *H04W 4/02* (2018.01)
(52) U.S. Cl.
  CPC .............. *B60Q 9/00* (2013.01); *H04W 4/023* (2013.01); *A61B 2503/22* (2013.01); *A61B 2560/0242* (2013.01)

(56) References Cited

FOREIGN PATENT DOCUMENTS

| | | |
|---|---|---|
| DE | 102014200780 A1 | 7/2015 |
| GB | 2542846 A | 4/2017 |
| JP | 5408240 B2 | 2/2014 |
| KR | 101887499 B1 | 8/2018 |
| TW | M501561 U | 5/2015 |
| WO | 2004001695 A1 | 12/2003 |

* cited by examiner

HEALTH ADVISORY ALERT SYSTEMS, MOBILE COMPUTING UNITS HAVING THE SAME, AND HEALTH ADVISORY ALERT METHODS

CROSS-REFERENCE TO RELATED APPLICATION

This application is a continuation application of U.S. patent application Ser. No. 17/097,467 filed on Nov. 13, 2020, which is incorporated herein by reference in its entirety including the specification, drawings and abstract.

TECHNICAL FIELD

The present specification relates to health advisory alert systems, mobile computing units, and health advisory alert methods, and more particularly, to health advisory alert systems, mobile computing units, and health advisory alert methods that notifies vehicle passengers when they should wear personal protective equipment.

BACKGROUND

Due to a rise in infectious diseases, such as COVID-19, many government agencies are either recommending or requiring people to wear personal protective equipment (PPE) such as face masks in certain situations. In addition, some people may elect to wear PPE in areas having a high level infectious diseases even if there is no government directive in place. However, different locations and jurisdictions may have different government directives and/or different levels of infectious disease, which may continually change. Accordingly, it may be difficult for people traveling in vehicles to be aware of local directives and/or disease levels at different locations.

Therefore, there is a need for a health advisory alert system to notify vehicle travelers of when it is recommended or required to wear PPE.

SUMMARY

In an embodiment, a health advisory alert system for a vehicle may include a controller configured to determine whether a vehicle occupant is preparing to exit the vehicle. Upon determination that the vehicle occupant is preparing to exit the vehicle, the controller may determine a location of the vehicle, determine a health advisory metric based on the location of the vehicle, and determine whether personal protective equipment should be worn based on the health advisory metric, and upon determination that personal protective equipment should be worn, output a notification to the vehicle occupant indicating that personal protective equipment should be worn.

In an embodiment, a mobile computing unit may include a controller configured to determine that a user is preparing to exit a vehicle. Upon determination that the user is preparing to exit the vehicle, the controller may determine a location of the mobile computing unit, determine a health advisory metric based on the location of the mobile computing unit, and determine whether personal protective equipment should be worn based on the health advisory metric. Upon determination that personal protective equipment should be worn, the controller may output a notification indicating that personal protective equipment should be worn.

In an embodiment, a health advisory alert method may include determining that a vehicle occupant is preparing to exit a vehicle and upon determination that the vehicle occupant is preparing to exit the vehicle, determining a location of the vehicle, determining a health advisory metric based on the location of the vehicle, determining whether personal protective equipment should be worn based on the health advisory metric, and upon determination that personal protective equipment should be worn, outputting a notification to the vehicle occupant indicating that personal protective equipment should be worn.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

The embodiments disclosed herein include health advisory alert systems. In one embodiment, when a driver parks a vehicle, a health advisory alert system may determine that the driver is about to exit the vehicle. The health advisory alert system may then determine a location of the vehicle and determine whether PPE should be worn in that location. This determination may be based on a pollution level in the area, a level of infectious disease in the area, or whether there are any government ordinances or regulations recommending or requiring that PPE be worn in the area.

When the health advisory alert system determines that PPE should be worn in the location where the vehicle is parked, the vehicle system may determine whether the driver and/or any other vehicle occupants are wearing PPE. The vehicle system may determine whether a vehicle occupant is wearing PPE by capturing an image of the vehicle occupant and performing image processing.

When the health advisory alert system determines that PPE should be worn in the location where the vehicle is parked and it is determined that the vehicle occupant is not wearing PPE, the health advisory alert system may output a notification to the vehicle occupant indicating that PPE should be worn. When the vehicle system determines that PPE should be worn in the location where the vehicle is parked and it is determined that all vehicle occupants are wearing PPE, the health advisory alert system may output a notification to the vehicle occupants to continue wearing PPE. Alternatively, when it is determined that the vehicle occupants are wearing PPE, the health advisory alert system may not provide additional notification regarding PPE. In embodiments, the health advisory alert system may output the notifications disclosed herein automatically.

In another embodiment, a mobile computing unit such as a smart phone may be used as part of a health advisory alert system. As such, a user may carry a mobile computing unit onto public transportation and still have access to the health advisory alert system.

In this embodiment, a mobile computing unit carried by a user may determine that the user is preparing to exit a vehicle. In some examples, the user may indicate that they are preparing to exit a vehicle by pressing a button or otherwise activating the mobile computing unit. The mobile computing unit may then determine a location of the mobile computing unit and determine whether PPE should be worn in the location where the user is preparing to exit the vehicle. When the mobile computing unit determines that PPE should be worn, the mobile computing unit may output a notification to the user indicating as much.

Figure 1:
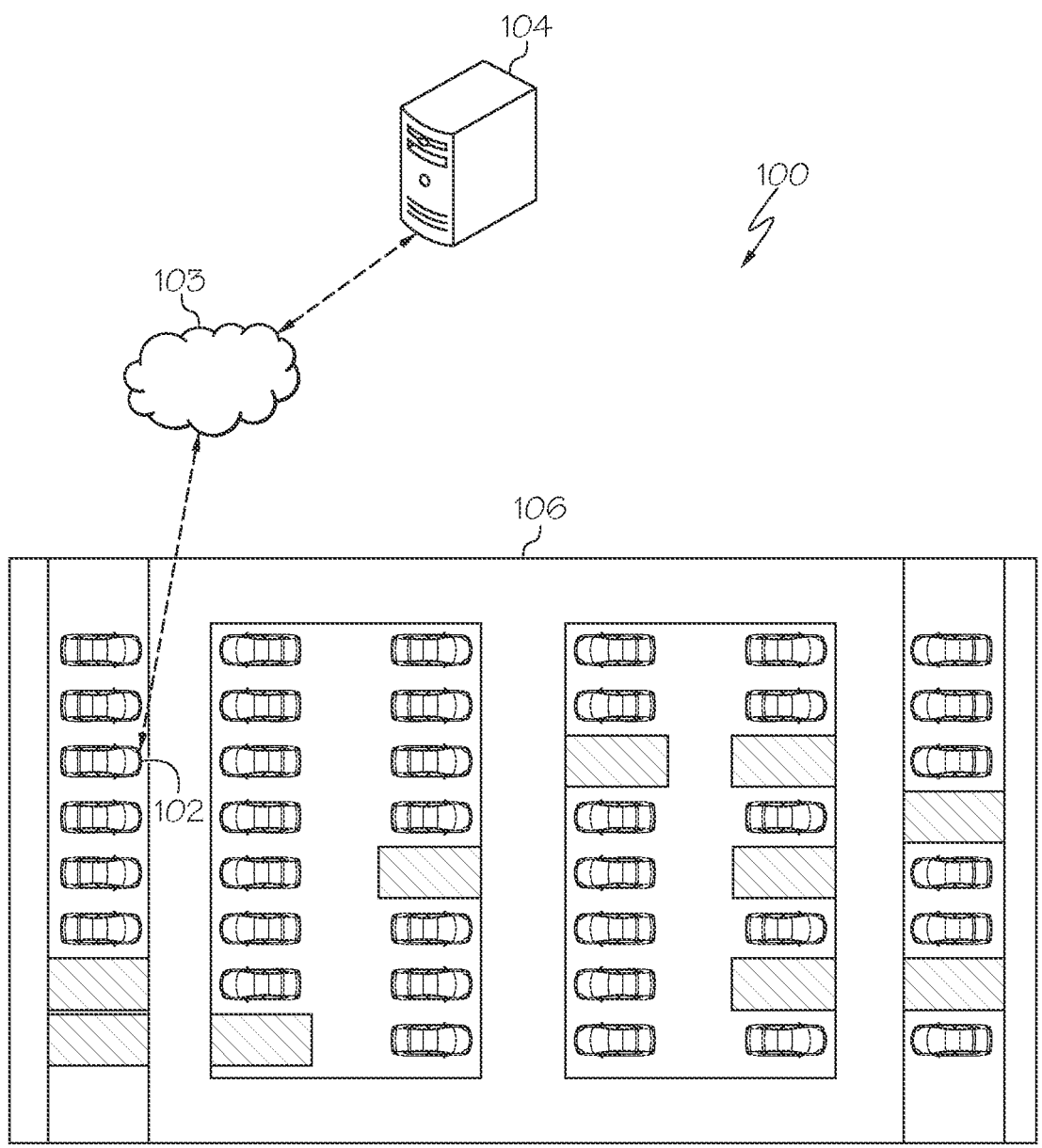
FIG. 1 schematically depicts an environment where an exemplary health advisory alert system may be utilized, according to one or more embodiments shown and described herein.

Referring to FIG. 1, a health advisory alert system is illustrated at 100. The system 100 includes a vehicle 102 and one or more servers 104. In the example of FIG. 1, a user parks the vehicle 102 in parking lot 106 and prepares to exit the vehicle 102. A health advisory alert system 200 (shown in FIG. 2) of the vehicle 102 may be communicatively coupled to the one or more servers 104. Although the example of FIG. 1 shows a single server 104, it should be understood that the health advisory alert system 200 may be communicatively coupled to multiple servers, as discussed in further detail below.

In the illustrated example, each of the servers 104 may comprise a fixed edge server (e.g., a road-side unit), a moving edge server (e.g., another vehicle), a cloud-based computing system, an Internet server, or any other suitable remote computing device. The health advisory alert system 200 of the vehicle 102 may send data to and receive data from a variety of servers, as discussed in further detail below.

Figure 2:
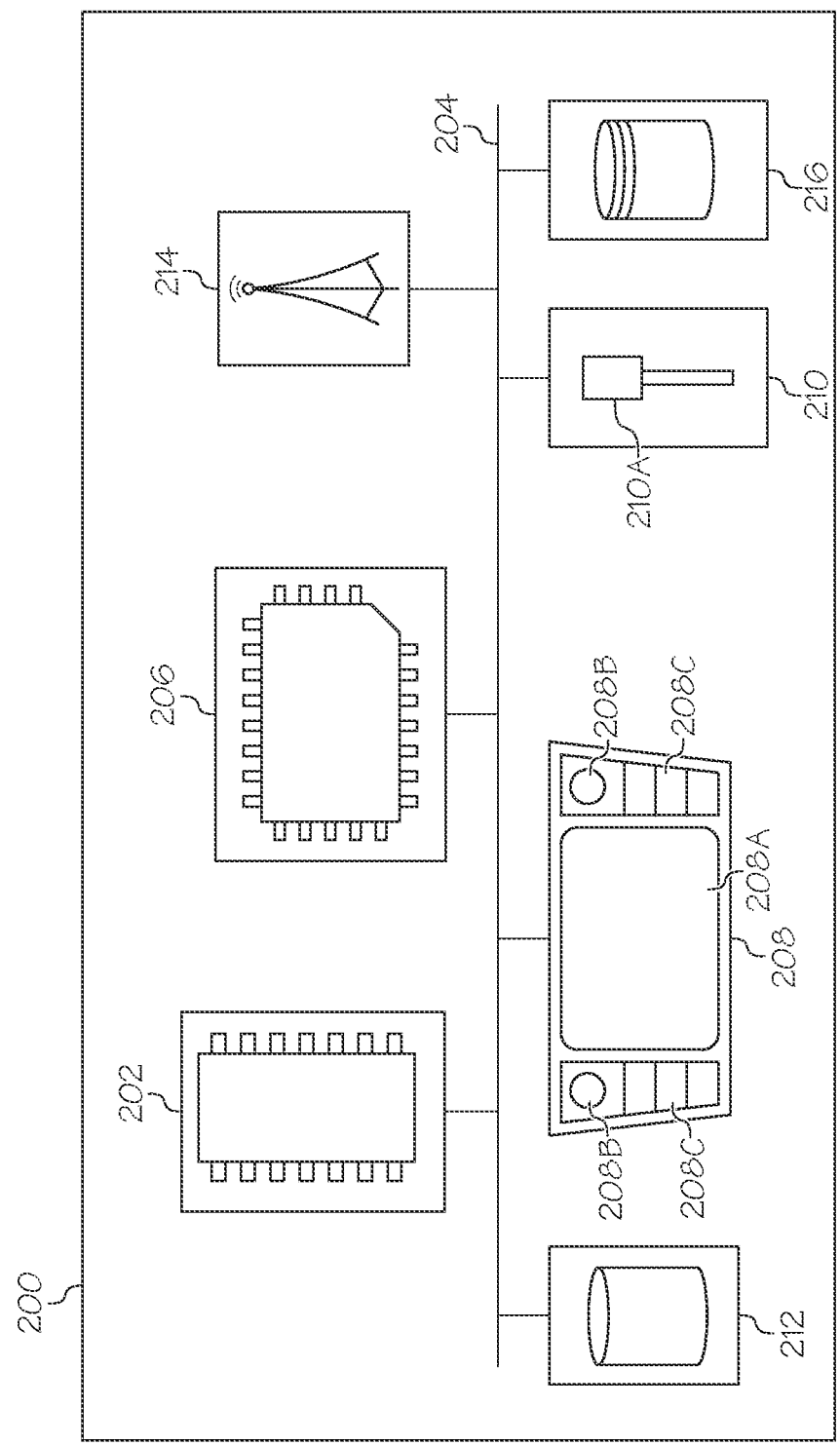
FIG. 2 depicts a schematic diagram of an exemplary health advisory alert system, according to one or more embodiments shown and described herein.

FIG. 2 depicts the health advisory alert system 200 included in the vehicle 102 of FIG. 1. The health advisory alert system 200 includes one or more processors 202, a communication path 204, one or more memory modules 206, a display unit 208, a global positioning system (GPS) unit 210, one or more vehicle sensors 212, network interface hardware 214, and a data storage component 216, the details of which will be set forth in the following paragraphs.

Each of the one or more processors 202 may be any device capable of executing machine readable and executable instructions. Accordingly, each of the one or more processors 202 may be a controller, an integrated circuit, a microchip, a computer, an electronic control unit, or any other computing device. The one or more processors 202 are coupled to a communication path 204 that provides signal interconnectivity between various modules of the health advisory alert system 200. Accordingly, the communication path 204 may communicatively couple any number of processors 202 with one another, and allow the modules coupled to the communication path 204 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 204 may be formed from any medium that is capable of transmitting a signal such as, for example, conductive wires, conductive traces, optical waveguides, or the like. In some embodiments, the communication path 204 may facilitate the transmission of wireless signals, such as Wi-Fi, Bluetooth®, Near Field Communication (NFC) and the like. Moreover, the communication path 204 may be formed from a combination of mediums capable of transmitting signals. In one embodiment, the communication path 204 comprises a combination of conductive traces, conductive wires, connectors, and buses that cooperate to permit the transmission of electrical data signals to components such as processors, memories, sensors, input devices, output devices, and communication devices. Accordingly, the communication path 204 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The health advisory alert system 200 includes one or more memory modules 206 coupled to the communication path 204. The one or more memory modules 206 may comprise RAM, ROM, flash memories, hard drives, or any device capable of storing machine readable and executable instructions such that the machine readable and executable instructions can be accessed by the one or more processors 202. The machine readable and executable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable and executable instructions and stored on the one or more memory modules 206. Alternatively, the machine readable and executable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

Referring still to FIG. 2, the health advisory alert system 200 comprises the display unit 208, which may output information to vehicle occupants and receive input from vehicle occupants. The display unit 208 may comprise a display 208A, one or more speakers 208B, and at least one input 208C. In the example of FIG. 2, the display 208A may display text and/or images to vehicle occupants. The speakers 208B may output audio to vehicle occupants. The input 208C may allow vehicle occupants to input information. In one example, the input 208C may comprise a touch screen.

In other examples, the input 208C may comprise a keyboard or another input device. In other examples, the health advisory alert system 200 may comprise a separate input device to allow a user to input information. In the illustrated example, the display unit 208 may output information related to PPE, as disclosed herein.

Referring still to FIG. 2, the health advisory alert system 200 comprises the GPS unit 210 coupled to the communication path 204 such that the communication path 204 communicatively couples the GPS unit 210 to other modules of the health advisory alert system 200. The GPS unit 210 may determine a location of the vehicle 102 using the GPS unit 210. In one embodiment, the GPS unit 210 may comprise a satellite antenna 210A configured to receive signals from GPS satellites. Specifically, in one embodiment, the satellite antenna 210A includes one or more conductive elements that interact with electromagnetic signals transmitted by GPS satellites. The received signal is transformed into a data signal indicative of the location (e.g., latitude and longitude) of the satellite antenna 210A or an object positioned near the satellite antenna 210A, by the one or more processors 202. Thus, the satellite antenna 210A allows the health advisory alert system 200 to determine the location of the vehicle 102. The location of the vehicle 102 may be used by the health advisory alert system 100 as disclosed herein.

The health advisory alert system 200 comprises one or more vehicle sensors 212. Each of the one or more vehicle sensors 212 is coupled to the communication path 204 and communicatively coupled to the one or more processors 202. The one or more vehicle sensors 212 may include, but are not limited to, LiDAR sensors, RADAR sensors, optical sensors (e.g., cameras, laser sensors, proximity sensors, location sensors (e.g., GPS modules)), and the like. In one example, the vehicle sensors 212 include an air quality sensor which may detect a level of pollution or air quality outside of the vehicle 102. In another example, the vehicle sensors 212 may include one or more internal vehicle cameras which may capture images of a driver or other occupants of the vehicle 102. In another example, the vehicle sensors 212 may include at least one sensor to determine whether a vehicle occupant is preparing to exit the vehicle 102 (e.g., an ignition switch sensor, a door lock sensor, a shift position sensor, and the like).

Still referring to FIG. 2, the health advisory alert system 200 comprises network interface hardware 214 for communicatively coupling the health advisory alert system 200 to the one or more servers 104. The network interface hardware 214 can be communicatively coupled to the communication path 204 and can be any device capable of transmitting and/or receiving data via a network. Accordingly, the network interface hardware 214 can include a communication transceiver for sending and/or receiving any wired or wireless communication. For example, the network interface hardware 214 may include an antenna, a modem, LAN port, Wi-Fi card, WiMax card, mobile communications hardware, near-field communication hardware, satellite communication hardware and/or any wired or wireless hardware for communicating with other networks and/or devices. In one embodiment, the network interface hardware 214 includes hardware configured to operate in accordance with the Bluetooth® wireless communication protocol. The network interface hardware 214 of the health advisory alert system 200 may receive a variety of data from the one or more servers 104 as disclosed herein.

In some embodiments, the health advisory alert system 200 may be communicatively coupled to the one or more servers 104 by a network 103. In one embodiment, the network may include one or more computer networks (e.g., a personal area network, a local area network, or a wide area network), cellular networks, satellite networks and/or a global positioning system and combinations thereof. Accordingly, the health advisory alert system 200 can be communicatively coupled to the network via a wide area network, via a local area network, via a personal area network, via a cellular network, via a satellite network, etc. Suitable local area networks may include wired Ethernet and/or wireless technologies such as, for example, wireless fidelity (Wi-Fi). Suitable personal area networks may include wireless technologies such as, for example, IrDA, Bluetooth®, Wireless USB, Z-Wave, ZigBee, and/or other near field communication protocols. Suitable cellular networks include, but are not limited to, technologies such as LTE, WiMAX, UMTS, CDMA, and GSM.

Still referring to FIG. 2, the health advisory alert system 200 comprises the data storage component 216 such as a database. The data storage component 216 may store data that may be utilized by the memory modules 206 and/or other components of the health advisory alert system 200. For example, the data storage component 216 may store data received by the one or more vehicle sensors 212.

Figure 3:
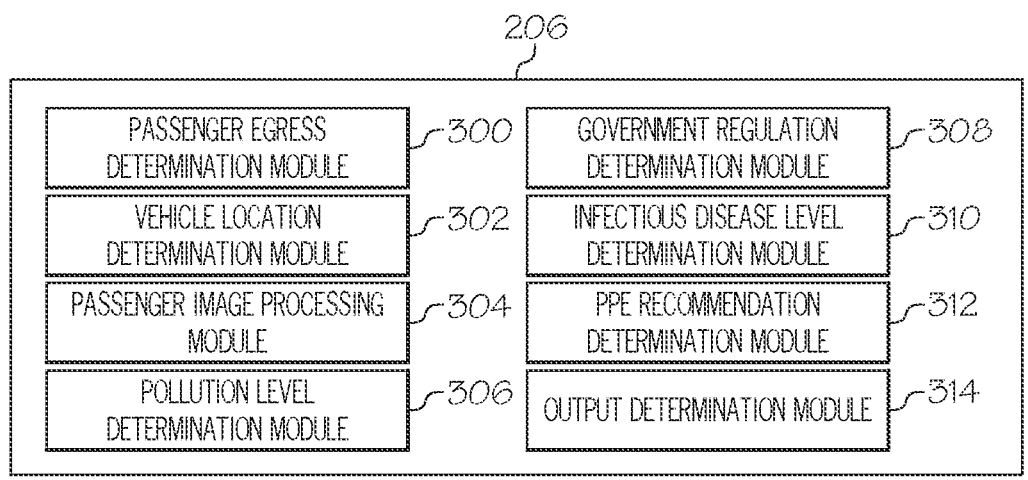
FIG. 3 depicts a schematic diagram of a plurality of memory modules that may be part of the health advisory alert system of FIG. 2, according to one or more embodiments shown and described herein.

Now referring to FIG. 3, exemplary memory modules 206 of the health advisory alert system 200 are shown. The one or more memory modules 206 include a passenger egress determination module 300, a vehicle location determination module 302, a passenger image processing module 304, a pollution level determination module 306, a government regulation determination module 308, an infectious disease level determination module 310, a PPE recommendation determination module 312, and an output determination module 314. Each of the passenger egress determination module 300, the vehicle location determination module 302, the passenger image processing module 304, the pollution level determination module 306, the government regulation determination module 308, the infectious disease level determination module 310, the PPE recommendation determination module 312, and the output determination module 314 may be a program module in the form of operating systems, application program modules, and other program modules stored in the one or more memory modules 206. Such a program module may include, but is not limited to, routines, subroutines, programs, objects, components, data structures and the like for performing specific tasks or executing specific data types as will be described below.

The passenger egress determination module 300 may determine when a driver or other vehicle occupants are preparing to exit the vehicle 102. In some examples, the passenger egress determination module 300 may determine that a vehicle occupant is preparing to exit the vehicle 102 based on data received from one or more of the vehicle sensors 212. In one example, the passenger egress determination module 300 may determine that a vehicle occupant is preparing to exit the vehicle 102 when the vehicle is put into park (e.g., based on data captured by a shift position sensor). In another example, the passenger egress determination module 300 may determine that a vehicle occupant is preparing to exit the vehicle 102 when the ignition of the vehicle 102 is turned off (e.g., based on data captured by an ignition switch sensor). In another example, the passenger egress determination module 300 may determine that a vehicle occupant is preparing to exit the vehicle 102 when the vehicle 102 has stopped and the doors have been unlocked (e.g., based on data captured by a door lock sensor). In another example, the passenger egress determination module 300 may determine that a vehicle occupant is preparing to exit the vehicle 102 when the vehicle stops at a particular location (e.g., a known location of the home or office of the owner of the vehicle 102). In another example, a vehicle occupant may utilize the input 208C to indicate that they are planning to exit the vehicle (e.g., an indicator to explicitly activate the health advisory alert system). In other examples, the passenger egress determination module 300 may utilize other methods to determine whether a vehicle occupant is preparing to exit the vehicle 102.

The vehicle location determination module 302 may determine the location of the vehicle 102. In one example, the vehicle location determination module 302 may determine the location of the vehicle 102 based on a GPS signal received by the GPS unit 210. In some examples, the vehicle location determination module 302 may determine the location of the vehicle 102 after the passenger egress determination module 300 determines that a vehicle occupant is preparing to exit the vehicle 102. In other examples, the vehicle location determination module 302 may determine the location of the vehicle 102 before the passenger egress determination module 300 determines whether a vehicle occupant is preparing to exit the vehicle 102.

The passenger image processing module 304 may determine whether a vehicle occupant is wearing PPE (e.g., a face mask, a face shield, or other face covering). More specifically, the passenger image processing module 304 may receive an image of one or more vehicle occupants captured by one or more of the vehicle sensors 212 (e.g., an internal vehicle camera). The passenger image processing module 304 may then analyze a captured image of a vehicle occupant (e.g., utilizing image processing techniques) to determine whether the vehicle occupant is wearing PPE.

The pollution level determination module 306 may determine a level of pollution or air quality outside of the vehicle 102. In one example, one of the vehicle sensors 212 may comprise an air quality detector that may analyze a sample of air around the vehicle 102. The pollution level determination module 306 may then determine a level of pollution based on the measurements performed by the air quality detector. For example, the pollution level determination module 306 may determine an air quality index (AQI) based on the data gathered by the air quality detector.

In other examples, the pollution level determination module 306 may receive data from a server (e.g., the server 104) indicating a level of pollution around the vehicle 102. For example, the pollution level determination module 306 may transmit the location of the vehicle 102, as determined by the vehicle location determination module 302, to a weather server 104 along with a request for the AQI in the area in which the vehicle 102 is located. The weather server 104 may then transmit the AQI back to the health advisory alert system 200 and the data may be received by the pollution level determination module 306. In other examples, the pollution level determination module 306 may determine a pollution level using one or more metrics other than AQI, such as smog index, pollen count, or the like.

The government regulation determination module 308 may determine whether there are any government ordinances or regulation requiring or recommending that PPE be worn within the area where the vehicle 102 is located. In some examples, the government regulation determination module 308 may transmit a request for such regulations to a server (e.g., the server 104) that maintains a list of regulations in force for the area where the vehicle 102 is located. In some examples, the government regulation determination module 308 may transmit a request to multiple servers representing different levels of government that have jurisdiction over the location where the vehicle 102 is located. For example, the government regulation determination module 308 may transmit a request to one server containing regulations of the city in which the vehicle 102 is located, another server containing regulations of the county in which the vehicle 102 is located, and another server containing regulations of the state in which the vehicle 102 is located. In some examples, the government regulation determination module 308 may look up such regulations using the World Wide Web or other Internet services.

The government regulation determination module 308 may receive information regarding PPE requirements or recommendations from one or more servers or Internet sources. The regulations may indicate that PPE is required to be worn or that PPE is recommended to be worn in a certain area. In some examples, the regulations may indicate that PPE is required to be worn only in certain situations (e.g., in public buildings or during certain times of the day). In some examples, the regulations may indicate the type of PPE that must be worn (e.g., face masks, face shields, and the like). In some examples, the government regulation determination module 308 may also determine other information related to public health (e.g., a recommendation to stay a certain distance away from other people, particular symptoms to look for, or testing locations for infectious diseases such as COVID-19 or other diseases).

The infectious disease level determination module 310 may determine a level of infectious or communicable disease in the area in which the vehicle 102 is located. In some examples, the infectious disease level determination module 310 may transmit a request for this information to a server (e.g., the server 104) that maintains such infectious disease information. In one example, the infectious disease level determination module 310 may transmit a request to a server maintained by the Center for Disease Control and Prevention (CDC) or other federal agencies or health organizations. In other examples, the infectious disease level determination module 310 may transmit a request to a server (e.g., the server 104) maintained by state or local health officials. In other examples, the infectious disease level determination module 310 may access one or more websites to determine a level of infectious disease in the area in which the vehicle 102 is located.

In one example, the infectious disease level determination module 310 may determine a level of COVID-19 in the area in which the vehicle 102 is located. However, in other examples, the infectious disease level determination module 310 may determine levels of other infectious disease. The infectious disease level determination module 310 may determine a number of metrics associated with the level of infectious disease in the area where the vehicle 102 is located including, a total number of cases of a particular disease, a number of cases of the disease per capita, a number of new cases of the disease during a particular time period (e.g., the last week or the last month), the rate at which cases of the disease are changing, or the reproduction rate Ro of the disease, among others metrics.

The PPE recommendation determination module 312 may determine whether PPE should be worn in the location in which the vehicle 102 is located. In particular, the PPE recommendation determination module 312 may determine a health advisory metric based on the location of the vehicle 102 and may determine whether PPE should be worn based on the determined health advisory metric.

In one example, the health advisory metric is the pollution level determined by the pollution level determination module 306 and the PPE recommendation determination module 312 may determine whether PPE should be worn based on the pollution level determined by the pollution level determination module 306. In one example, the health advisory metric is based on the pollution level determined by the pollution level determination module 306 and the PPE recommendation determination module 312 may determine whether PPE should be worn based on the health advisory metric. The PPE recommendation determination module 312 may determine that PPE should be worn when the determined pollution level is above a predetermined threshold or when the determined air quality is below a predetermined threshold. For example, the PPE recommendation determination module 312 may determine that PPE should be worn when the smog level determined by the pollution level determination module 306 is above a predetermined threshold level or when the AQI determined by the pollution level determination module 306 is below a predetermined threshold. In some examples, one or more of the thresholds described above may be set by a user using the input 208C of the display unit 208. In these examples, a user may specify a level of pollution or air quality they are comfortable with before the PPE recommendation determination module 312 recommends that PPE be worn.

In another example, the health advisory metric is whether any government regulations exist that require or recommend that PPE be worn, as determined by the government regulation determination module 308, and the PPE recommendation determination module 312 may determine whether PPE should be worn based on whether any government regulations exist that require or recommend that PPE be worn, as determined by the government regulation determination module 308. In one example, the health advisory metric is based on whether any government regulations exist that require or recommend that PPE be worn, as determined by the government regulation determination module 308 and the PPE recommendation determination module 312 may determine whether PPE should be worn based on the health advisory metric. In some examples, the PPE recommendation determination module 312 determines that PPE should be worn only when a government regulation requires that PPE be worn. In other examples, the PPE recommendation determination module 312 determines that PPE should be worn when a government regulation merely recommends that PPE be worn.

In another example, the health advisory metric is the level of infectious disease determined by the infectious disease level determination module 310 and the PPE recommendation determination module 312 may determine whether PPE should be worn based on the level of infectious disease determined by the infectious disease level determination module 310. In one example, the health advisory metric is based on the level of infectious disease determined by the infectious disease level determination module 310 and the PPE recommendation determination module 312 may determine whether PPE should be worn based on the health advisory metric. In one example, the PPE recommendation determination module 312 may determine that PPE should be worn when a particular metric determined by the infectious disease level determination module 310 exceeds a threshold. For example, the PPE recommendation determination module 312 may recommend that PPE should be worn when the number of cases of a disease per capita is above a certain threshold or when the number of cases is increasing by an amount greater than a threshold amount. In other examples, the PPE recommendation determination module 312 may determine whether PPE should be worn based on other metrics determined by the infectious disease level determination module 310.

In one example, the health advisory metric is a particular metric determined by the infectious disease level determination module 310 and the PPE recommendation determination module 312 may determine that PPE should be worn when the particular metric is above a predetermined threshold. In another example, the PPE recommendation determination module 312 may determine that PPE should be worn when the particular metric determined by the infectious disease level determination module 310 is above a user selected threshold. In some examples, the PPE recommendation determination module 312 may determine that PPE should be worn when a particular metric determined by the infectious disease level determination module 310 is above a threshold determined based on characteristics of a user. For example, a user may enter their age, gender, any pre-existing health conditions, or risk factors or personal information and the PPE recommendation determination module 312 may determine an appropriate threshold based on the information entered by the user.

In some examples, the health advisory metric is a combination of information determined by the pollution level determination module 306, the government regulation determination module 308, and the infectious disease level determination module 310 and the PPE recommendation determination module 312 may determine whether PPE should be worn based on the health advisory metric. For example, the PPE recommendation determination module 312 may determine that PPE should be worn when the pollution level determined by the pollution level determination module 306 is above a threshold amount, or when the government regulation determination module 308 determines that a government regulation requires the wearing of PPE, or when the infectious disease level determination module 310 determines that a level of infectious disease is above a threshold. In some examples, a user may select which criteria the PPE recommendation determination module 312 should use to determine whether PPE should be worn. For example, a user may select that the PPE should be recommended based on government regulations and infectious disease level but not based on pollution.

The output determination module 314 may cause the display unit 208 to output a notification regarding whether PPE should be worn, as determined by the PPE recommendation determination module 312. In some examples, the output determination module 314 may cause the display 208A to display text or images indicating that PPE should be worn when the PPE recommendation determination module 312 determines that PPE should be worn. In other examples, the output determination module 314 may cause the speakers 208B to output an audible notification regarding whether PPE should be worn. In some examples, the output determination module 314 may cause both the display 208A and the speakers 208B to output notifications regarding whether PPE should be worn.

In some examples, the output determination module 314 may cause the display unit 208 to output more specific information about wearing PPE. For example, the display unit 208 may output whether PPE is required to be worn by government regulations or only recommended to be worn. The display unit 208 may output certain conditions during which PPE must be worn (e.g., inside public buildings). The display unit 208 may also indicate why PPE should be worn (e.g., based on pollution, government regulations, or disease level).

In some examples, the output determination module 314 may cause the display unit 208 to indicate that PPE should be worn only when the PPE recommendation determination module 312 determines that PPE should be worn and the passenger image processing module 304 determines that one or more vehicle occupants are not wearing PPE. In some examples, when the PPE recommendation determination module 312 determines that PPE should be worn and the passenger image processing module 304 determines that the vehicle occupants are wearing PPE, the output determination module 314 may cause the display unit 208 to indicate that PPE should continue to be worn. In some examples, when the PPE recommendation determination module 312 determines that PPE need not be worn and the passenger image processing module 304 determines that the vehicle occupants are wearing PPE, the output determination module 314 may cause the display unit 208 to indicate that PPE may be taken off.

In the illustrated example, the output determination module 314 causes the display 208A to display information regarding whether PPE should be worn. However, in other examples, the output determination module 314 may cause the speakers 208B to output audio indicative of whether PPE should be worn. In some examples, when the PPE recommendation determination module 312 determines that PPE should be worn and the passenger image processing module 304 determines that one or more vehicle occupants are not wearing PPE, the output determination module 314 may lock the doors of the vehicle 102 until a vehicle occupant acknowledges that PPE will be worn (e.g., by making a selection using the input 208C).

Figure 4:
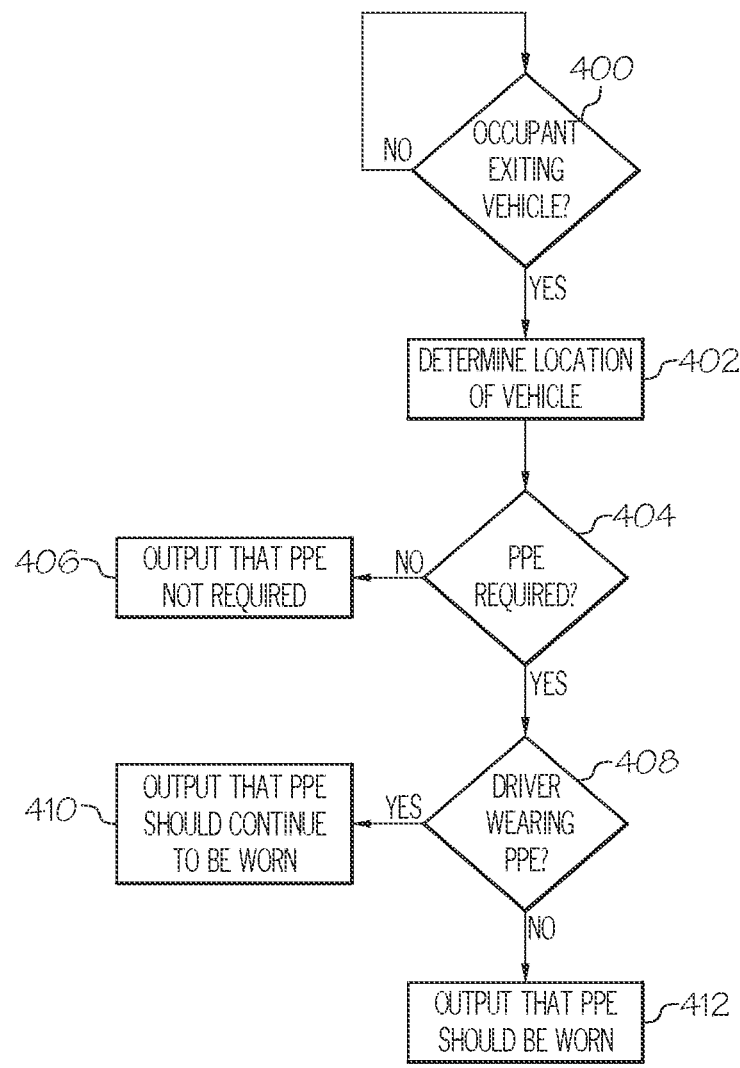
FIG. 4 depicts a flowchart of a method for operating the vehicle system of FIGS. 1-3, according to one or more embodiments shown and described herein.

FIG. 4 depicts a flowchart of an example method for operating the example health advisory alert system 200 of the health advisory alert system 100, according to one or more embodiments shown and described herein. At step 400, the passenger egress determination module 300 may determine whether a vehicle occupant is preparing to exit the vehicle 102. When the passenger egress determination module 300 determines that a vehicle occupant is not preparing to exit the vehicle 102 (no at step 400), then control returns to step 400. As such, the passenger egress determination module 300 may continually determine whether a vehicle occupant is preparing to exit the vehicle 102 until it is determined that a vehicle occupant is preparing to exit the vehicle 102. When the passenger egress determination module 300 determines that a vehicle occupant is preparing to exit the vehicle (yes at step 400), then control passes to step 402.

At step 402, the vehicle location determination module 302 may determine a location of the vehicle 102. The vehicle location determination module 302 may determine the location of the vehicle 102 based on a GPS signal received by the GPS unit 210.

At step 404, the PPE recommendation determination module 312 may determine whether PPE (e.g., face masks) should be worn by vehicle occupants based on a health advisory metric. The health advisory metric may be determined based on the location of the vehicle 102 determined by the vehicle location determination module 302. In one example, the health advisory metric may be based on a determination made by the pollution level determination module 306 (e.g., a determined AQI). In another example, the health advisory metric may be based on a determination made by the government regulation determination module 308 (e.g., whether government regulations require that PPE be worn). In another example, the health advisory metric may be based on a determination made by the infectious disease level determination module 310 (e.g., a number of cases of an infectious disease per capita).

The pollution level determination module 306 may determine a level of pollution or air quality at the location of the vehicle 102. The government regulation determination module 308 may determine whether any government regulations require or recommend that individuals in the vicinity of the location of the vehicle 102 wear PPE. The infectious disease level determination module 310 determines a level of one or more infectious diseases in the area around the location that the vehicle 102 is located. The PPE recommendation determination module 312 may determine that PPE should be worn when the pollution level determined by the pollution level determination module 306 is above a threshold level, when the level of infectious disease determined by the infectious disease level determination module 310 is above a threshold level, or when the government regulation determination module 308 determines that one or more government regulations recommend or require the wearing of PPE.

When the PPE recommendation determination module 312 determines that PPE is not required (no at step 404), then, at step 406, the output determination module 314 may cause the display unit 208 to indicate that PPE is not required to be worn. When the PPE recommendation determination module 312 determines that PPE should be worn (yes at step 404), then control passes to step 408.

At step 408, the passenger image processing module 304 may determine whether one or more occupants of the vehicle 102 are wearing PPE. In particular, an interior vehicle camera may capture an image of one or more occupants of the vehicle 102 and the passenger image processing module 304 may determine whether each occupant of the vehicle 102 is wearing PPE based on the captured image of each occupant (e.g., using image processing techniques). When the passenger image processing module 304 determines that occupants of the vehicle 102 are wearing PPE (yes at step 408), then, at step 410, the output determination module 314 may cause the display unit 208 to indicate that PPE should continue to be worn. When the passenger image processing module 304 determines that occupants of the vehicle 102 are not wearing PPE (no at step 408), then, at step 412, the output determination module 314 may cause the display unit 208 to indicate that PPE should be worn.

Figure 5:
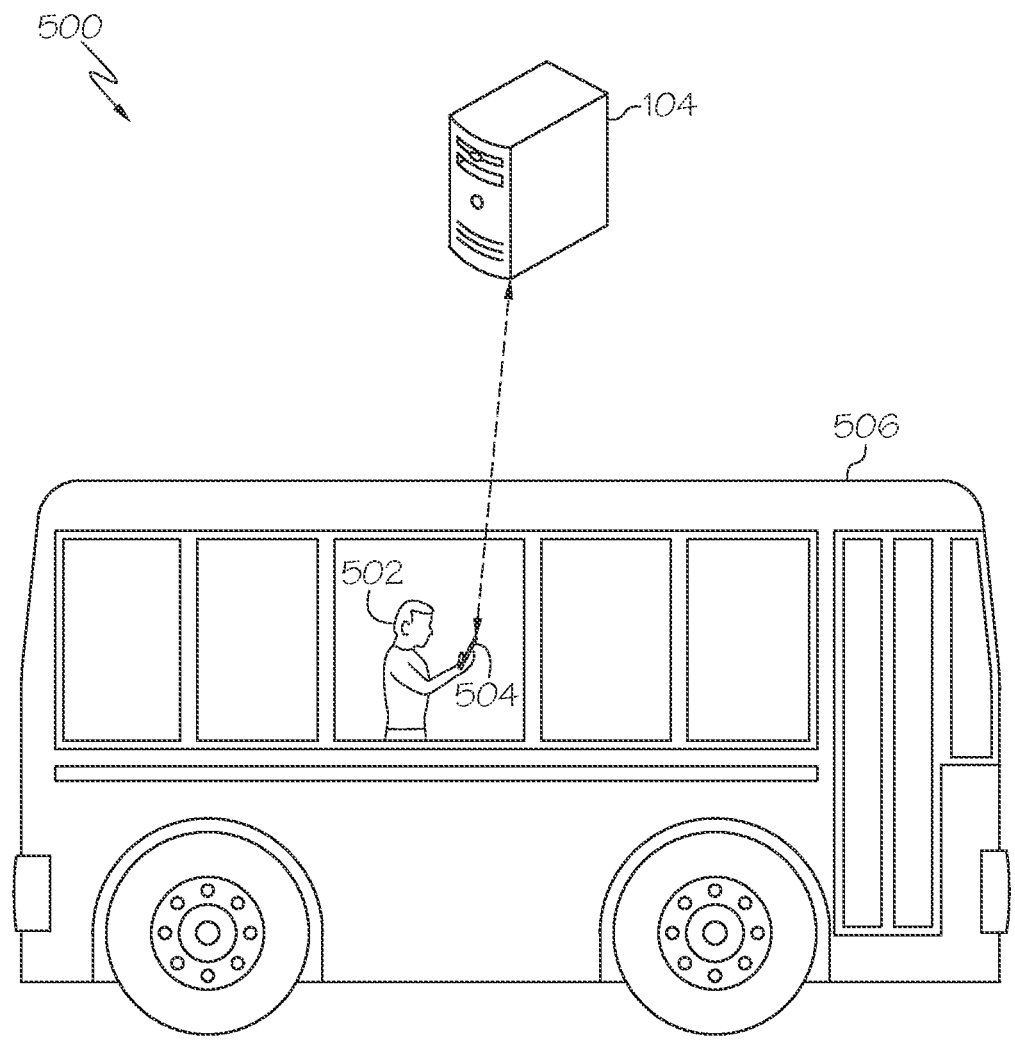
FIG. 5 schematically depicts another exemplary health advisory alert system, according to one or more embodiments shown and described herein.

Referring to FIG. 5, another embodiment of the health advisory alert system is generally illustrated at 500. The system 500 includes a passenger 502 carrying a mobile computing unit 504 while riding a public transportation vehicle 506, such as a bus, a plane, a train, a boat, a rideshare vehicle, a trolley, and the like. The system 500 further includes the one or more servers 104. The system 500 is similar to the system 100 except that the functions of the health advisory alert system 200 of the vehicle 102 of FIG. 1 may be performed by the mobile computing unit 504, as disclosed herein. Accordingly, in the example of FIG. 5, the passenger 502 may carry the mobile computing unit 504 on public transportation such as the public transportation vehicle 506. The passenger 502 may also carry the mobile computing unit 504 in other vehicles such as a train or an automobile that may not be equipped with the health advisory alert system 200 of FIG. 2.

In the example of FIG. 5, the passenger 502 carries the mobile computing unit 504 while riding on the public transportation vehicle 506. In other examples, the passenger 502 may carry the mobile computing unit 504 on other vehicles or other modes of transportation. When the public transportation vehicle 506 arrives at the desired destination of the passenger 502, the passenger 502 may utilize the mobile computing unit 504 to determine whether PPE should be worn, as disclosed herein. In the example of FIG. 5, the mobile computing unit 504 may be communicatively coupled to the one or more servers 104.

Figure 6:
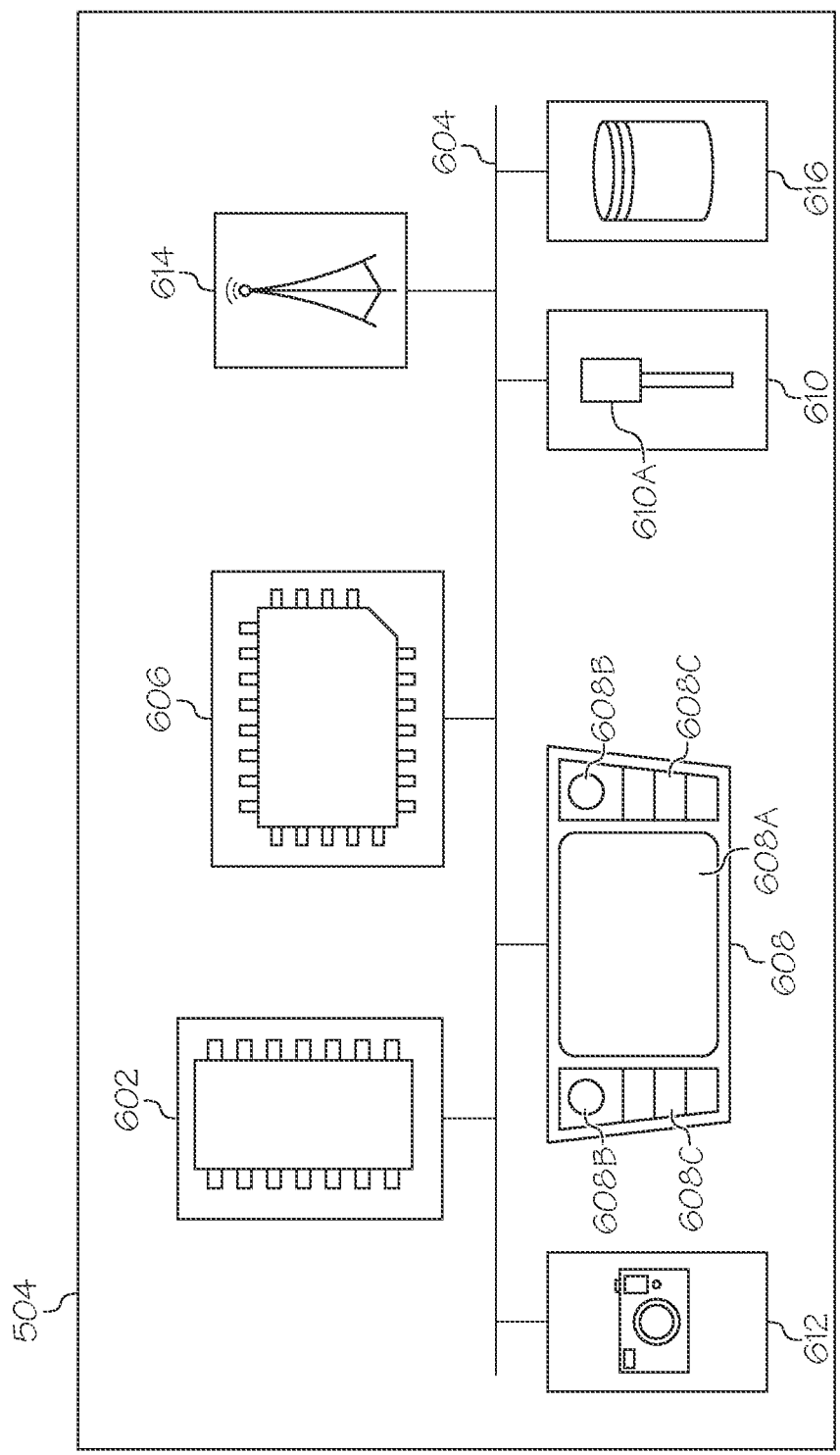
FIG. 6 depicts a schematic diagram of a mobile computing unit that may be part of the health advisory alert system of FIG. 5, according to one or more embodiments shown and described herein.

FIG. 6 depicts a schematic diagram of the mobile computing unit 504 of FIG. 5. In the illustrated example, the mobile computing unit 504 comprises a smart phone. However, in other examples the mobile computing unit 504 may comprise a table, a laptop computer, a smart watch, or any other portable electronic device. As shown in FIG. 6, the mobile computing unit 504 includes one or more processors 602, a communication path 604, one or more memory modules 606, a display unit 608, a GPS unit 610, a camera 612, network interface hardware 614, and a data storage component 616, the details of which will be set forth in the following paragraphs.

Each of the one or more processors 602 may be any device capable of executing machine readable and executable instructions. The one or more processors 602 may be similar to the one or more processors 202 of FIG. 2.

The one or more processors 602 are coupled to a communication path 604 that provides signal interconnectivity between various modules of the mobile computing unit 504. The communication path 604 may be similar to the communication path 204 of FIG. 2.

The mobile computing unit 504 includes one or more memory modules 606 coupled to the communication path 604. The one or more memory modules 606 may be similar to the one or more memory modules 206 of FIG. 2. The one or more memory modules 606 are described in further detail below with respect to FIG. 7.

The mobile computing unit 504 comprises a display unit 608 for outputting information to the passenger 502 and receiving information from the passenger 502. The display unit 608 may comprise a display 608A, one or more speakers 608B, and inputs 608C. In the illustrated example, the mobile computing unit 504 comprises a smart phone and the display 608A may comprise a screen of the smart phone, the speakers 608B may comprise a speaker of the smart phone, and the inputs 608C may comprise a keyboard and/or touch screen of the smart phone.

The mobile computing unit 504 comprises a GPS unit 610 coupled to the communication path 604 such that the communication path 604 communicatively couples the GPS unit 610 to other modules of the mobile computing unit 504. The GPS unit 610 may determine a location of the mobile computing unit 504 based on GPS data. In one example, the GPS unit 610 may comprise a satellite antenna 610A configured to receive signals from (GPS) satellites. The GPS unit 610 may be similar to the GPS unit 210 of FIG. 2, The mobile computing unit 504 comprises a camera 612. In the illustrated example, the camera 612 comprises a built-in camera of a smart phone. The camera 612 may capture an image of the passenger 502.

The mobile computing unit 504 comprises network interface hardware 614 for communicatively coupling the mobile computing unit 504 to the one or more servers 104. The network interface hardware 614 may be similar to the network interface hardware 214 of FIG. 2.

The mobile computing unit 504 comprises a data storage component 616. The data storage component 616 may store data that may be utilized by the memory modules 606 and/or other components of the mobile computing unit 504.

Figure 7:
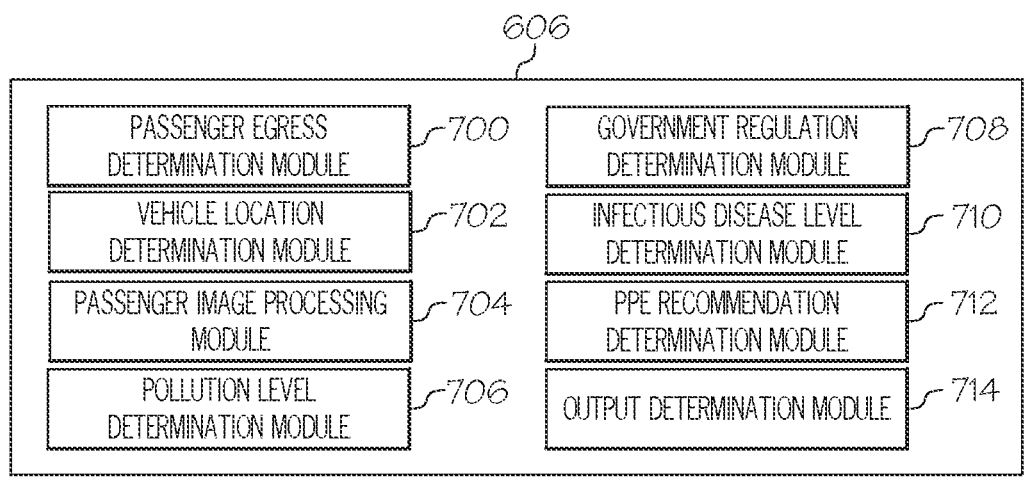
FIG. 7 depicts a schematic diagram of a plurality of memory modules that may be part of the mobile computing unit of FIG. 6.

Now referring to FIG. 7, exemplary memory modules 606 of the mobile computing unit 504 are shown. The one or more memory modules 606 include a passenger egress determination module 700, a mobile device location determination module 702, a passenger image processing module 304, a pollution level determination module 706, a government regulation determination module 708, an infectious disease level determination module 710, a PPE recommendation determination module 712, and an output determination module 714.

The passenger egress determination module 700 may determine whether the passenger 502 is preparing to exit a vehicle (e.g., the public transportation vehicle 506 in the example of FIG. 5). In one example, the passenger 502 may press a button on the mobile computing unit 504 to indicate that they are preparing to exit a vehicle. In other examples, the passenger egress determination module 700 may determine that the passenger 502 is preparing to exit the vehicle when the mobile computing unit 504 is near certain predetermined locations (e.g., the home or office of the passenger 502).

The mobile device location determination module 702 may determine the location of the mobile computing unit 504. In one example, the mobile device location determination module 702 may determine the location of the mobile computing unit 504 based on a GPS signal received by the GPS unit 610.

The passenger image processing module 704 may determine whether the passenger 502 is wearing PPE. More specifically, the passenger image processing module 704 may receive an image of the passenger 502 captured by the camera 612. The passenger image processing module 704 may then analyze the captured image (e.g., utilizing image processing techniques) to determine whether the passenger 502 is wearing PPE.

The pollution level determination module 706 may determine a level of pollution of air quality in the area around the location of the mobile computing unit 504. In one example, the pollution level determination module 706 may determine a level of pollution in the area around the location of the mobile computing unit 504 by querying a server (e.g., a weather server) and retrieving information from the server.

The government regulation determination module 708 may determine whether any government ordinances or regulations are in place that require or recommend that PPE be worn in the area around the location of the mobile computing unit 504. The government regulation determination module 708 may perform this function in a similar manner as the government regulation determination module 308 of FIG. 3.

The infectious disease level determination module 710 may determine a level of infectious disease in the area around the location of the mobile computing unit 504. The infectious disease level determination module 710 may perform this function in a similar manner as the infectious disease level determination module 310 of FIG. 3.

The PPE recommendation determination module 712 may determine whether the passenger 502 should wear PPE after exiting the vehicle they are traveling in (e.g., the public transportation vehicle 506). In particular, the PPE recommendation determination module 712 may determine a health advisory metric based on the location of the mobile computing unit 504 and may determine whether PPE should be worn based on the determined health advisory metric. The PPE recommendation determination module 712 may determine the health advisory metric based on the determinations made by the pollution level determination module 706, the government regulation determination module 708, and/or the infectious disease level determination module 710. The PPE recommendation determination module 712 may perform this function in a similar manner as the PPE recommendation determination module 312 of FIG. 3.

The output determination module 714 may cause the display unit 608 to output information regarding whether PPE should be worn. The output determination module 714 may perform this function in a similar manner as the output determination module 314 of FIG. 3.

Figure 8:
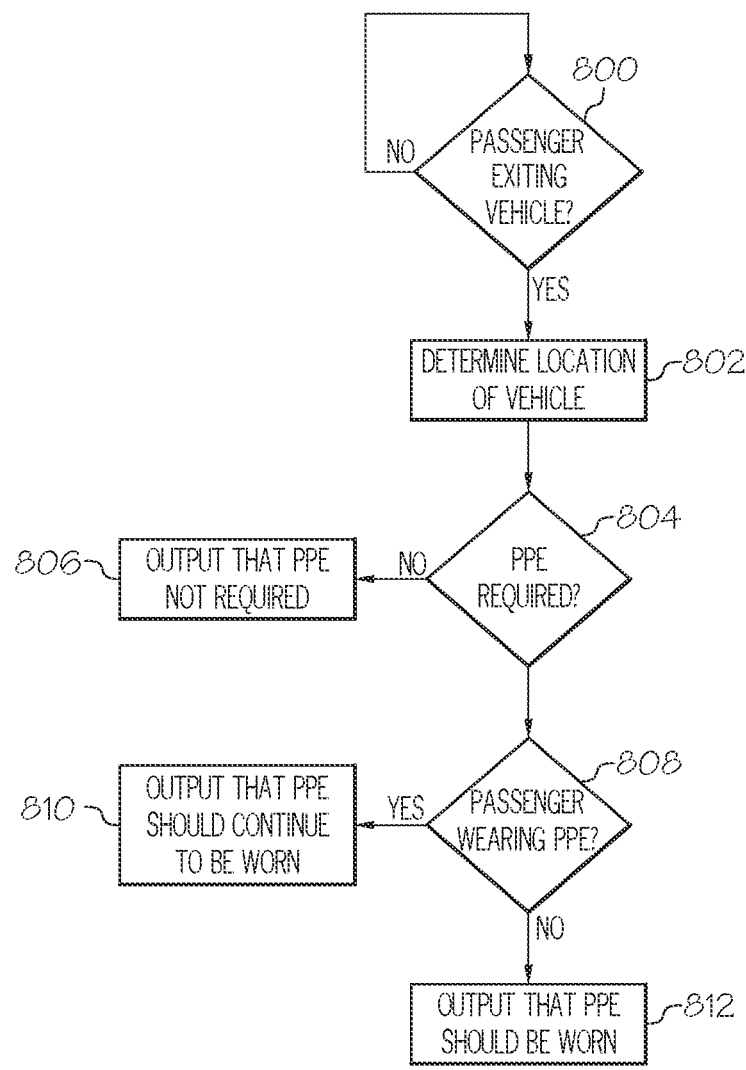
FIG. 8 depicts a flowchart of a method for operating the mobile computing unit of FIGS. 5-7, according to one or more embodiments shown and described herein.

FIG. 8 depicts a flowchart of an example method for operating the example mobile computing unit 504 of the health advisory alert system 500, according to one or more embodiments shown and described herein. At step 800, the passenger egress determination module 700 may determine whether a passenger (e.g., the passenger 502 of FIG. 5) is preparing to exit a vehicle (e.g., the public transportation vehicle 506 of FIG. 5). When the passenger egress determination module 700 determines that the passenger is not preparing to exit the vehicle (no at step 800), then control returns to step 800. As such, the passenger egress determination module 700 may continually determine whether the passenger is preparing to exit the public transportation vehicle 506 until is determined that the passenger is preparing to exit the public transportation vehicle 506. When the passenger egress determination module 700 determines that the passenger is preparing to exit the vehicle (yes at step 800), then control passes to step 802.

At step 802, the mobile device location determination module 702 may determine a location of the mobile computing unit 504. The mobile device location determination module 702 may determine the location of the mobile computing unit 504 based on a GPS signal received by the GPS unit 610.

At step 804, the PPE recommendation determination module 712 may determine whether PPE (e.g., a face mask) should be worn by the passenger 502 based on a health advisory metric. The health advisory metric may be determined based on the location of the mobile computing unit 504 determined by the mobile device location determination module 702. In one example, the health advisory metric may be based on a determination made by the pollution level determination module 706 (e.g., a determined AQI). In another example, the health advisory metric may be based on a determination made by the government regulation determination module 708 (e.g., whether government regulations require that PPE be worn). In another example, the health advisory metric may be based on a determination made by the infectious disease level determination module 710 (e.g., a number of cases of an infectious disease per capita).

The pollution level determination module 706 may determine a level of pollution or air quality at the location of the mobile computing unit 504. The government regulation determination module 708 may determine whether any government regulations require or recommend that individuals in the vicinity of the location of the mobile computing unit 504 wear PPE. The infectious disease level determination module 710 determines a level of one or more infectious diseases in the area around the location of the mobile computing unit 504. The PPE recommendation determination module 712 may determine that PPE should be warn when the pollution level determined by the pollution level determination module 706 is above a threshold level, when the level of infectious disease determined by the infectious disease level determination module 710 is above a threshold level, or when the government regulation determination module 708 determines that one or more government regulations recommend or require the wearing of PPE.

When the PPE recommendation determination module 712 determines that PPE is not required (no at step 804), then, at step 806, the output determination module 714 may cause the display unit 608 to indicate that PPE is not required to be worn. When the PPE recommendation determination module 712 determines that PPE should be worn (yes at step 804), then control passes to step 808.

At step 808, the passenger image processing module 704 may determine whether the passenger 502 is wearing PPE. In particular, the camera 612 of the mobile computing unit 504 may capture an image of the passenger 502 and the passenger image processing module 704 may determine whether the passenger 502 is wearing PPE based on the captured image (e.g., using image processing techniques).

When the passenger image processing module 704 determines that the passenger 502 is wearing PPE (yes at step 808), then, at step 810, the output determination module 714 may cause the display unit 608 to indicate that PPE should continue to be worn. When the passenger image processing module 704 determines that the passenger 502 is not wearing PPE (no at step 808), then, at step 812, the output determination module 714 may cause the display unit 608 to indicate that PPE should be worn.

It should be understood that embodiments described herein are directed to a health advisory alert system. When a driver parks a vehicle, the health advisory alert system may determine that the driver is preparing to exit the vehicle. The health advisory alert system may then determine the location of the vehicle using GPS. After determining the location of the vehicle, the health advisory alert system may determine whether PPE should be worn in the area around where the vehicle is located. The health advisory alert system may determine whether PPE should be worn based on government regulations governing the area, a determined level of pollution in the area, or a determined infectious disease level in the area.

When the health advisory alert system determines that PPE should be worn based on the location of the vehicle, an interior vehicle camera may capture an image of the driver. The health advisory alert system may then determine whether the driver is wearing PPE based on the captured image. When the driver is not wearing PPE, the health advisory alert system may output a notification to the driver to wear the appropriate PPE.

In another embodiment, a mobile computing unit carried by a passenger in a vehicle may determine that the passenger is preparing to exit the vehicle. The mobile computing unit may then determine the location of the mobile computing unit using GPS. After determining the location of the mobile computing unit, the mobile computing unit may determine whether PPE should be worn at that location. This determination may be based on government regulations governing the area, a determined level of pollution in the area, or a determined infectious disease level in the area. When the mobile computing unit determines that PPE should be worn, the mobile computing unit may display an indication that PPE should be worn.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A health advisory alert method comprising:
   determining whether a vehicle occupant is preparing to exit a vehicle; and
   upon determination that the vehicle occupant is preparing to exit the vehicle,
   determining a location of the vehicle;
   determining a level of infectious disease associated with the location of the vehicle based on data received from a server;
   determining a health advisory metric based on the location of the vehicle and the determined level of infectious disease associated with the location of the vehicle;
   determining whether personal protective equipment should be worn based on the health advisory metric; and
   upon determination that personal protective equipment should be worn, outputting a notification to the vehicle occupant indicating that personal protective equipment should be worn.

2. The method of claim 1, further comprising:
   determining whether the vehicle occupant is wearing personal protective equipment; and
   upon determination that the vehicle occupant is not wearing personal protective equipment, outputting the notification to the vehicle occupant indicating that personal protective equipment should be worn.

3. The method of claim 1, further comprising:
   upon determination that the vehicle occupant is wearing personal protective equipment and upon determination that personal protective equipment should be worn, outputting a notification to the vehicle occupant indicating that the personal protective equipment should continue to be worn.

4. The method of claim 1, further comprising:
   upon determination that the vehicle occupant is wearing personal protective equipment and upon determination that personal protective equipment should not be worn, outputting a notification to the vehicle occupant indicating that the personal protective equipment may be taken off.

5. The method of claim 1, further comprising:
   capturing an image of the vehicle occupant; and
   determining whether the vehicle occupant is wearing personal protective equipment based on the image of the vehicle occupant.

6. The method of claim 1, further comprising:
   in response to the notification, causing a display unit to output a visual or audio notification indicating that personal protective equipment should be worn.

7. The method of claim 1, further comprising:
   determining that personal protective equipment should be worn when the determined level of infectious disease is above a user selected threshold.

8. A health advisory method comprising:
   determining whether a vehicle occupant is preparing to exit a vehicle; and
   upon determination that the vehicle occupant is preparing to exit the vehicle,
   determining a location of the vehicle;
   determining a level of pollution associated with the location of the vehicle based on data received from a server;
   determining a health advisory metric based on the location of the vehicle and the determined level of pollution associated with the location of the vehicle;
   determining whether personal protective equipment should be worn based on the health advisory metric; and
   upon determination that personal protective equipment should be worn, outputging a notification to the vehicle occupant indicating that personal protective equipment should be worn.

9. The method of claim 8, further comprising:
   determining whether the vehicle occupant is wearing personal protective equipment; and
   upon determination that the vehicle occupant is not wearing personal protective equipment, outputting the notification to the vehicle occupant indicating that personal protective equipment should be worn.

10. The method of claim 8, further comprising:
    upon determination that the vehicle occupant is wearing personal protective equipment and upon determination that personal protective equipment should be worn, outputting a notification to the vehicle occupant indicating that the personal protective equipment should continue to be worn.

11. The method of claim 8, further comprising:
    upon determination that the vehicle occupant is wearing personal protective equipment and upon determination that personal protective equipment should not be worn, outputting a notification to the vehicle occupant indicating that the personal protective equipment may be taken off.

12. The method of claim 8, further comprising:
    capturing an image of the vehicle occupant; and
    determining whether the vehicle occupant is wearing personal protective equipment based on the image of the vehicle occupant.

13. The method of claim 8, further comprising:
    in response to the notification, causing a display unit to output a visual or audio notification indicating that personal protective equipment should be worn.

14. A health advisory alert method comprising:
    determining whether a vehicle occupant is preparing to exit the vehicle; and
    upon determination that the vehicle occupant is preparing to exit the vehicle,
    determining a location of the vehicle;
    determining whether any government ordinances associated with the location of the vehicle require that personal protective equipment be worn based on data received from a server;
    determining a health advisory metric based on the location of the vehicle and the determination as to whether any government ordinances associated with the location of the vehicle require that personal protective equipment be worn;
    determining whether personal protective equipment should be worn based on the health advisory metric; and
    upon determination that personal protective equipment should be worn, outputting a notification to the vehicle occupant indicating that personal protective equipment should be worn.

15. The method of claim 14, further comprising:
determining whether the vehicle occupant is wearing personal protective equipment; and
upon determination that the vehicle occupant is not wearing personal protective equipment, outputting the notification to the vehicle occupant indicating that personal protective equipment should be worn.

16. The method of claim 14, further comprising:
upon determination that the vehicle occupant is wearing personal protective equipment and upon determination that personal protective equipment should be worn, outputting a notification to the vehicle occupant indicating that the personal protective equipment should continue to be worn.

17. The method of claim 14, further comprising:
upon determination that the vehicle occupant is wearing personal protective equipment and upon determination that personal protective equipment should not be worn, outputting a notification to the vehicle occupant indicating that the personal protective equipment may be taken off.

18. The method of claim 14, further comprising:
capturing an image of the vehicle occupant; and
determining whether the vehicle occupant is wearing personal protective equipment based on the image of the vehicle occupant.

19. The method of claim 14, further comprising:
in response to the notification, causing a display unit to output a visual or audio notification indicating that personal protective equipment should be worn.

* * * * *

UNITED STATES PATENT AND TRADEMARK OFFICE
CERTIFICATE OF CORRECTION

| | |
|---|---|
| PATENT NO. | : 11,688,266 B2 |
| APPLICATION NO. | : 17/578993 |
| DATED | : June 27, 2023 |
| INVENTOR(S) | : Bryan Else Yamasaki, Timothy Wang and Roger Akira Kyle |

It is certified that error appears in the above-identified patent and that said Letters Patent is hereby corrected as shown below:

On the Title Page

Item (56), U.S. patent documents, cite No. 2, delete "Kanukurthy" and insert
-- Kanukurthy et al. --, therefor.

In the Claims

In Column 18, Line(s) 16, Claim 8, delete "outputging" and insert -- outputting --, therefor.

Signed and Sealed this
Eighth Day of August, 2023

Katherine Kelly Vidal
*Director of the United States Patent and Trademark Office*